US010695458B2

(12) United States Patent
Bradford et al.

(10) Patent No.: US 10,695,458 B2
(45) Date of Patent: Jun. 30, 2020

(54) ABSORBENT MATERIALS

(71) Applicant: ADVANCED MEDICAL SOLUTIONS LIMITED, Winsford, Cheshire (GB)

(72) Inventors: Colin Raymond Bradford, Keighley (GB); Brian John Hamerslagh, Higher Runcorn (GB)

(73) Assignee: ADVANCED MEDICAL SOLUTIONS LIMITED, Winsford (GB)

( * ) Notice: Subject to any disclaimer, the term of this patent is extended or adjusted under 35 U.S.C. 154(b) by 109 days.

(21) Appl. No.: 15/653,848

(22) Filed: Jul. 19, 2017

(65) Prior Publication Data

US 2018/0021472 A1   Jan. 25, 2018

(30) Foreign Application Priority Data

Jul. 20, 2016 (GB) .................................. 1612572.6

(51) Int. Cl.
| | | |
|---|---|---|
| *A61L 15/60* | (2006.01) | |
| *A61L 15/32* | (2006.01) | |
| *A61F 13/02* | (2006.01) | |
| *A61L 26/00* | (2006.01) | |
| *A61F 13/00* | (2006.01) | |
| *D04H 1/4382* | (2012.01) | |

(52) U.S. Cl.
CPC .......... *A61L 15/60* (2013.01); *A61F 13/0253* (2013.01); *A61L 15/32* (2013.01); *A61L 26/0023* (2013.01); *A61L 26/0052* (2013.01); *A61F 2013/00421* (2013.01); *D04H 1/4382* (2013.01)

(58) Field of Classification Search
CPC ........ A61F 13/0253; A61F 2013/00421; A61F 15/32; A61F 15/60; A61F 26/0023; A61F 26/0052; D04H 1/4382
See application file for complete search history.

(56) References Cited

U.S. PATENT DOCUMENTS

| | | | |
|---|---|---|---|
| 3,810,280 A | | 5/1974 | Walton et al. |
| 4,500,585 A | | 2/1985 | Erickson |
| 4,704,113 A | * | 11/1987 | Schoots ............ A61F 13/00008 602/45 |
| 5,520,673 A | * | 5/1996 | Yarbrough ............ A61F 13/511 604/358 |
| 5,820,874 A | * | 10/1998 | Mahoney ................ A61K 9/70 424/443 |
| 5,830,496 A | * | 11/1998 | Freeman ........... A61F 13/00029 424/445 |
| 2003/0120229 A1 | * | 6/2003 | de Jong ............ A61F 13/00987 604/367 |
| 2017/0305105 A1 | * | 10/2017 | Poruthoor ........... B32B 37/0046 |

FOREIGN PATENT DOCUMENTS

| | | | |
|---|---|---|---|
| EP | 2659865 A1 * | 11/2013 | ....... A61F 13/00029 |
| GB | 1 370 888 A | 10/1974 | |
| WO | WO 2007/079502 | 7/2007 | |

OTHER PUBLICATIONS

Dec. 7, 2017 Extended European Search Report issued in European Application 17182177.0.

* cited by examiner

*Primary Examiner* — Arti Singh-Pandey
(74) *Attorney, Agent, or Firm* — Nixon & Vanderhye P.C.

(57) ABSTRACT

The present invention provides dry-creped absorbent material comprised of gelling fibres intended for use particularly, but not necessarily exclusively, as wound dressings or as a component (absorbent substrate) of a wound dressing, as well as wound dressings comprising the absorbent material.

19 Claims, No Drawings

ABSORBENT MATERIALS

The present application claims the benefit of GB Patent Application No. 1612572.6 filed 20 Jul. 2016, the entire contents of which is incorporated herein by reference.

The present invention relates to absorbent materials intended for use particularly, but not necessarily exclusively, as wound dressings or as a component (absorbent substrate) of a wound dressing. More particularly the invention relates to absorbent materials comprised of gelling fibres.

Gelling fibres are, as their name suggests, fibres that form a gel when in contact with an aqueous fluid. As examples of gelling fibres, there may be mentioned alginates, carboxymethyl cellulose, carboxymethyl viscose, carboxymethyl chitosan, sulphonated cellulose and sulphonated viscose. Within any one type of gelling fibre, the method by which the fibre has been produced can effect the degree of gelling. Thus, for example, the degree of gelling of alginate fibres is dependent on the type of alginate from which the fibre is produced and cations used to precipitate (coagulate) the alginate fibres during the spinning process by which they are produced, whereas the degree of gelling for carboxymethyl cellulose and sulphonated fibres is dependent on the degree of carboxymethylation or sulphonation respectively.

Wound dressings comprising an absorbent material comprised of gelling fibres and, for example, in the form of a non-woven felt may be used for application to highly exuding wounds since the gelling fibres absorb the aqueous exudate from the wound to form a gel which helps to maintain a moist environment for promoting wound healing and which can be removed relatively easily from the wound when required. Ideally the gel has sufficient we strength so that it can be removed intact from the wound. As such, the absorbent material should have a relatively high wet strength. Generally, materials produced using low gelling fibres will have a high wet strength, whilst materials produced using high gelling fibres will have a low wet strength.

Wet strength of absorbent materials to be used for wound dressings can be increased by calendering. During calendering, the substrate is passed through the calendering rollers (one or both of which can be heated) and as a result will be flattened and possibly also bonded if it contains a thermoplastic component. However, calendering significantly reduces the absorbency of the material and potentially the speed at which it can absorb exudate. To minimise this effect, one of the calender rollers can be engraved with a pattern so that contact of the roller with the substrate is limited to defined areas (i.e. the technique frequently referred to as "point bonding"). This prevents overall flattening of the substrate and reduces (but does not eliminate entirely) the negative effects of the calender.

An alternative method of improving the wet strength of absorbent materials, e.g. non-woven felts containing high gelling fibres, is to sew threads through the material. However stitching, particularly if excessive, can reduce both absorbency and speed of absorption, i.e. the same disadvantage obtained with calendering. Moreover sewing incorporates threads into the absorbent substrate and these could create points to which cells are capable of adhering, making the dressing more difficult to remove. Also, for very high gelling materials, the gelled material can slide off the threads (so-called "fish boning") during removal so that the gelled material has to be separately washed out of the wound.

It is an object of the present invention to obviate or mitigate the abovementioned disadvantages.

According to a first aspect of the present invention there is provided a dry-creped absorbent material comprised of gelling fibres.

Dry creping is a technique in which creping folds are formed in a material and "set" (to form the finished crepe structure) using a combination of heat and pressure and is effected under totally dry conditions. Dry creping is to be contrasted with wet creping processes, in which a liquid (such as an adhesive) is used to set the creped material. Wet creping techniques are not suitable for the production of substrate materials for use in the present invention since the gelling fibre component would simply cause the liquid to become absorbed in the material and so preventing the folds from becoming set.

Generally dry creping is effected by passing a travelling web around a heated roller and into a creping cavity which retards the travel of a moving web of material so that the material gathers into concertina-like folds. The heat and pressure applied to the material causes the folds to become "set" in the sense that they do not simply collapse (thereby allowing the crepe structure to be retained) but nevertheless allow the material to stretch by opening of the folds. During the dry creping process, the pressure and temperature at the creping points increase the strength of the material. Surprisingly we have found that absorbent dry-creped substrates comprised of gelling fibres are capable, when wetted with an aqueous fluid, of increasing in length (by opening of the creping folds) substantially to the uncreped length without the application of any tension.

Surprisingly also we have found that the tensile strength of the creped material that has been wetted and returned to its original length is greater than that of the equivalent material that has not been creped. This combination of properties renders the materials ideally suited for use as, or as components of, wound dressings.

The dry-creped substrate is typically a non-woven material. Preferably, the dry-creped substrate is a non-woven fibrous material, for example a felt (preferably a needled, non-woven felt). In embodiments, the material/substrate does not incorporate stitching.

Dry-creped substrates in accordance with the invention are preferably produced with a compaction ratio of 80-40%, the compaction ratio being the length of the creped material expressed as a percentage of the length of the uncreped material from which it is produced. Thus, in the case of the preferred compaction ratio of 80-40%, a 10 cm creped length is formed from 12.5 cm (80%) to 25 cm (40%) of uncreped material. Dry-creped materials in accordance with the invention preferably have a stretch ratio of 30-100%, the stretch ratio being the ratio of the length by which the creped material may be extended to the point where it "locks out" or where damage starts to occur to the original length of the creped material expressed as a percentage. ("Lock-out" is the point where the folds of the creped material are all just opened). Thus, in the case of the preferred stretch ratio of 30-100%, a 10 cm creped length of substrate would stretch to a length of 13 cm (for 30%) or to 20 cm (for 100%).

Dry-creped substrates of the invention may be produced from the appropriate non-creped precursor material (e.g. an uncreped non-woven felt) using a so-called bladeless dry creping apparatus, an example of which is disclosed in U.S. Pat. No. 3,810,280. A particularly suitable bladeless dry-creper is available from Micrex Corporation, Walpole, Mass., USA under their designation "Bladeless Cavity Creper".

Briefly, the "Bladeless Cavity Creper" comprises a heated roller with a fine textured surface and a creping assembly located adjacent to, but spaced from, the peripheral surface of the roller. The arrangement is such that a creping cavity is defined, on the one hand, by a retarder element (a component of the creping arrangement) and the peripheral surface of the roller. Material to be creped is passed around the roller but its movement is retarded on a passage into the creping cavity so the material gathers into folds and is creped.

Controls are the texture/frictional properties of the retarder, the height of the cavity, the heated roller temperature, and the speed of processing. Additionally, the speed that the creped substrate is wound up affects the finished properties in terms of the compaction ratio and stretch ratio. The faster the wind up, the lower the compaction ratio, and the lower stretch properties in the final substrate. Reducing the wind up speed increases the compaction ratio, and increases the stretch properties. However, it is necessary to have some tension to pull the substrate from the creping packaging. For further information see WO2007/079502.

Gelling fibres suitable for use in the wound dressings of the present invention include alginate fibres, polyacrylates, carboxymethylcellulose (CMC) fibres, carboxymethyl viscose, sulphonated cellulose (SC) fibres, sulphonated viscose, carboxymethyl chitosan fibres and other carboxymethylated/sulphonated fibres. In embodiments, the gelling fibres comprise alginate fibres. Optionally, the alginate fibres may incorporate carboxymethyl cellulose. Alternatively, the gelling fibres may be sulphonated fibres. In embodiments wherein the gelling fibres are sulphonated fibres, the sulphonated fibres may comprise sulphonated cellulose or sulphonated viscose, e.g. sulphonated cellulose.

The degree of gelling provided by the gelling fibres can be controlled by the conditions under which the fibres are manufactured. The degree of gelling of alginate fibres, for example, can be modified by appropriate selection of the type of alginate used, and by the salts used to coagulate the fibres during the spinning processes used to create said fibres. The degree of gelling of CMC or SC fibres can be modified by adjusting the extent of carboxymethylation or sulphonation of the cellulose fibres from which the CMC or SC fibres are derived. Carboxymethylation and sulphonation processes can also be applied to fibres other than cellulose in order to increase absorbance and degree of gelling of those fibres.

The gelling fibres of the wound dressing may comprise superabsorbent fibres such as polyacrylates (e.g. Oasis manufactured by Technical Absorbents Ltd). Superabsorbent fibres have higher absorbency as compared with other gelling fibres.

Dry creped substrates for use in wound dressings according to the invention may be comprised solely of gelling fibres or may comprise an admixture of both gelling and non-gelling fibres, the latter (if present) normally constituting less than 50% by weight of the total weight of the gelling and non-gelling fibres. Thus, in embodiments, the material of the invention may comprise up to 50% by weight of non-gelling fibres. The use of non-gelling fibres can be advantageous for tailoring the dry and/or wet strength of the substrate. Examples of non-gelling fibres that may be used include, but are not limited to cotton, viscose, polyester, nylon and polypropylene.

In embodiments of the invention, the fibres in the substrate may have a length of 25-100 mm. Thus, the gelling fibres and/or non-gelling fibres may have a length of 25-100 mm. In embodiments of the invention, the fibres in the substrate may have a thickness of 1.5-5.0 dtex. Thus, the gelling fibres and/or non-gelling fibres may have a thickness of 1.5-5.0 dtex. Generally the fibres (gelling and/or non-gelling) in the substrate will have a length of 25-100 mm and a thickness of 1.5-5.0 dtex.

The dry creped absorbent materials (comprising gelling fibres) in accordance with the invention have a number of advantages.

Dry-creped materials in accordance with the invention comprise a plurality of parallel, concertina like folds which can be opened to allow the substrate to be stretched on application of a stretching force transverse to the length of the corrugations and subsequently relaxed to its original length when the stretching force is released. In addition to enhanced "stretchiness", the dry-creped substrate is generally softer and more drapeable than the uncreped material from which it is produced.

As detailed above, the materials are such that, when wetted with an aqueous fluid, they are capable of increasing in length (by opening of the creping folds) substantially to the uncreped length without the application of any tension. Furthermore the tensile strength of the creped material that has been wetted and returned to its original length is greater than that of the equivalent material that has not been creped. Further advantages are detailed below.

It is a particular advantage that the materials in accordance with the invention have a high wet strength without the need to incorporate stitching. Thus, in embodiments, the material/substrate of the invention does not incorporate stitching.

Although the dry-creped material may only be capable of absorbing to 100% saturation a lower total amount of aqueous fluid than the uncreped material from which it is produced (the reduction in absorbency being due to the compression effected during the dry-creping process), it is nevertheless the case that the dry-creped substrate will usually have at least the same absorbency as measured on a gram per unit area basis than the original uncreped material. For absorbent substrates used in wound dressing, absorbency is commonly measured as $g/100$ $cm^2$. Two opposing factors come into play in determining the relative absorbency (expressed on a weight per unit area basis) of the dry creped substrate as compared to the uncreped material from which it is produced. On the one hand, the area of the dry creped material (as determined by length×width) will be less than that of the uncreped material. On the other hand, there is some reduction in the inherent absorbency of the dry creped material (as compared to the uncreped material) due to the aforementioned compression in the dry creping process. Generally, this second factor does not outweigh the first factor, so that the absorbency (expressed on a weight per unit area basis) of the dry creped material will generally be at least that of the uncreped material.

The above summarised properties render the materials of the invention suitable for use in wound dressings in various applications.

The absorbent material for use in a wound dressing may be cut (to the appropriate size) from a web of the dry-creped material. If a rectangular strip of absorbent material is cut in the machine direction of the web (so that the corrugations extend across the width of the strip) then the absorbent material will increase in length when wetted with an aqueous fluid. Alternatively, if a rectangular strip of absorbent material is cut in the cross-direction from the web (so that the corrugations extend parallel to the length of the strip) then the absorbent material will increase in width when wetted with aqueous fluid.

Depending on the particular application, the wound dressing may comprise only the dry-creped material or may comprise the dry-creped substrate in combination with other components conventionally used in wound dressings, e.g. an adhesive layer or an adhesive substrate to hold the absorbent material in place.

The combination of stretch/relaxation and wet strength properties of the material (i.e. summarised above as (i) and (ii)) render the material useful as a wound dressing that has to cope with body movement, e.g. knee, hip, elbow etc.

For such applications, the wound dressing will generally comprise the dry-creped substrate in combination with either an adhesive material or an adhesive layer to hold it in place.

Optionally, the dry-creped substrate of any embodiment described herein further comprises an antimicrobial agent, preferably a compound of a metal such as silver, copper or zinc; an iodine based compound; polyhexamethylene biguanide (PHMB) and derivatives; or octenidine and derivatives. If present, the antimicrobial agent will typically comprise silver in ionic form (typically in an amount of 0.5-3.0%), PHMB (typically in an amount of 0.5-2.0%), zinc as zinc oxide (typically in an amount up to 10%), iodine (typically in an amount of 0.5-2.0%), or octenidine (typically in an amount of 0.5-2.0%), the percentages being based on the weight of the dry-creped substrate.

The antimicrobial agent is preferably incorporated in the fibres which comprise the dry-creped substrate during the production of those fibres. This may be achieved when producing alginate fibres, for example, by incorporating the antimicrobial into an aqueous dope comprising the alginate material, and by spinning that aqueous dope to produce fibres having an antimicrobial agent incorporated therein.

Thus, in line with the above discussion, the present disclosure provides the following numbered embodiments:
1. A dry-creped absorbent material comprised of gelling fibres.
2. A material as described in embodiment 1 having a compaction ratio of 80 to 40%.
3. A material as described in embodiment 1 or 2 having a stretch ratio of 30 to 100%.
4. A material as described in any one of embodiments 1 to 3 wherein the gelling fibres comprise alginate fibres.
5. A material as described in embodiment 4 wherein the alginate fibres incorporate carboxymethyl cellulose.
6. A material as described in any one of embodiments 1 to 3 wherein the gelling fibres comprise carboxymethyl cellulose, carboxymethyl viscose or carboxymethyl chitosan.
7. A material as described in any one of embodiments 1 to 3 wherein the gelling fibres are sulphonated fibres.
8. A material as described in embodiment 7 wherein the sulphonated fibres comprise sulphonated cellulose or sulphonated viscose.
9. A material as described in any one of embodiments 1 to 3 wherein the gelling fibres comprise super absorbent fibres.
10. A material as described in any one of embodiments 1 to 9 wherein the gelling fibres incorporate an antimicrobial agent.
11. A material as described in any one of embodiments 1 to 10 wherein the gelling fibres have a length of 25 to 100 mm.
12. A material as described in any one of embodiments 1 to 11 wherein the gelling fibres have a thickness of 1.5 to 5.0 dtex.
13. A material as described in any one of embodiments 1 to 12 further comprising up to 50% by weight of non-gelling fibres.
14. A material as described in embodiment 13 wherein the non-gelling fibres have a length of 25 to 100 mm.
15. A material as described in embodiment 13 or 14 wherein the non-gelling fibres have a thickness of 1.5 to 5.0 dtex.
16. A material as described in any one of embodiments 1 to 15 wherein the absorbent substrate is a non-woven material.
17. A material as described in embodiment 16 wherein the non-woven material is a felt.
18. A material as described in any one of embodiments 1 to 17 wherein the material does not incorporate stitching.
19. A wound dressing comprising an absorbent material as described in any one of embodiments 1 to 18.

The invention claimed is:

1. A dry-creped absorbent material comprised of gelling fibres.

2. A material as claimed in claim 1 having a compaction ratio of 80 to 40%.

3. A material as claimed in claim 1 having a stretch ratio of 30 to 100%.

4. A material as claimed in claim 1 wherein the gelling fibres comprise alginate fibres.

5. A material as claimed in claim 4 wherein the alginate fibres incorporate carboxymethyl cellulose.

6. A material as claimed in claim 1 wherein the gelling fibres comprise carboxymethyl cellulose, carboxymethyl viscose or carboxymethyl chitosan.

7. A material as claimed in claim 1 wherein the gelling fibres are sulphonated fibres.

8. A material as claimed in claim 7 wherein the sulphonated fibres comprise sulphonated cellulose or sulphonated viscose.

9. A material as claimed in claim 1 wherein the gelling fibres comprise super absorbent fibres.

10. A material as claimed in claim 1 wherein the gelling fibres incorporate an antimicrobial agent.

11. A material as claimed in claim 1 wherein the gelling fibres have a length of 25 to 100 mm.

12. A material as claimed in claim 1 wherein the gelling fibres have a thickness of 1.5 to 5.0 dtex.

13. A material as claimed in claim 1 further comprising up to 50% by weight of non-gelling fibres.

14. A material as claimed in claim 13 wherein the non-gelling fibres have a length of 25 to 100 mm.

15. A material as claimed in claim 13 wherein the non-gelling fibres have a thickness of 1.5 to 5.0 dtex.

16. A material as claimed in claim 1 wherein the absorbent substrate is a non-woven material.

17. A material as claimed in claim 16 wherein the non-woven material is a felt.

18. A material as claimed in claim 1 wherein the material does not incorporate stitching.

19. A wound dressing comprising an absorbent material as claimed in claim 1.

* * * * *